United States Patent
Brunner et al.

[11] Patent Number: 5,829,723
[45] Date of Patent: Nov. 3, 1998

[54] MEDICAL DEVICE MOUNTING STRUCTURE

[75] Inventors: Glenn D. Brunner, Dublin; Charles R. Patzer, Ashville, both of Ohio

[73] Assignee: Medex, Inc., Hilliard, Ohio

[21] Appl. No.: 495,923

[22] Filed: Jun. 28, 1995

[51] Int. Cl.⁶ .................................................. A47B 96/06
[52] U.S. Cl. .............................. 248/222.13; 248/229.15; 5/658
[58] Field of Search ........................ 248/221.11, 222.13, 248/229.12, 229.15, 229.25, 229.22, 230.6, 231.41, 219.4; 5/658, 503.1

[56] References Cited

U.S. PATENT DOCUMENTS

| | | | |
|---|---|---|---|
| 190,651 | 5/1877 | Webster . | |
| D. 269,121 | 5/1983 | Pollard | D24/31 |
| D. 283,441 | 4/1986 | Vcelka et al. | D24/53 |
| 594,035 | 11/1897 | Reichert . | |
| 944,312 | 12/1909 | Brede . | |
| 1,303,345 | 5/1919 | McFeaters . | |
| 2,156,025 | 4/1939 | Paul . | |
| 2,371,433 | 3/1945 | Davis . | |
| 2,473,908 | 6/1949 | Rubin . | |
| 2,557,430 | 6/1951 | Hensley et al. | 248/102 |
| 2,638,301 | 5/1953 | Smith | 248/229 |
| 2,732,159 | 1/1956 | Connors et al. | 248/224 |
| 2,762,595 | 9/1956 | Jenne | 248/224 |
| 2,876,027 | 3/1959 | Sulmonetti | 287/54 |
| 3,081,023 | 3/1963 | Taylor | 232/24 |
| 3,269,550 | 8/1966 | Marcus | 211/87 |
| 3,429,450 | 2/1969 | Lambert | 211/60 |
| 3,452,954 | 7/1969 | Lucietto et al. | 248/220.5 |
| 3,544,060 | 12/1970 | Stoltz et al. | 251/9 |
| 3,581,929 | 6/1971 | Guenard et al. | 220/22 |
| 3,599,828 | 8/1971 | Conway et al. | 220/102 |
| 3,747,166 | 7/1973 | Eross | 24/81 |
| 3,797,792 | 3/1974 | Huber | 248/229 |
| 3,901,231 | 8/1975 | Olson | 128/244 F |
| 3,915,189 | 10/1975 | Holbrook et al. | 137/205 |
| 4,017,050 | 4/1977 | Rosenau | 248/222.13 |
| 4,030,690 | 6/1977 | Hanauer et al. | 248/311.3 |
| 4,093,076 | 6/1978 | Newton | 211/74 |
| 4,099,626 | 7/1978 | Magnussen, Jr. | 211/60 R |
| 4,113,217 | 9/1978 | O'Connell | 248/221.3 |
| 4,115,966 | 9/1978 | DeLee | 52/148 |
| 4,132,380 | 1/1979 | Pastore | 248/224.1 |
| 4,182,367 | 1/1980 | Day | 137/557 |
| 4,211,380 | 7/1980 | Lillegard et al. | 248/229 |

(List continued on next page.)

FOREIGN PATENT DOCUMENTS

| | | |
|---|---|---|
| 0077151 | 9/1982 | European Pat. Off. . |
| 1049697 | 1/1952 | France . |
| 1467702 | 2/1966 | France . |
| 2619151 | 4/1977 | Germany . |
| 1375949 | 4/1974 | United Kingdom . |
| WO9207396 | 4/1992 | WIPO . |
| WO9310835 | 6/1993 | WIPO . |
| WO9404113 | 3/1994 | WIPO . |
| WO9509026 | 6/1995 | WIPO . |

*Primary Examiner*—Ramon O. Ramirez
*Assistant Examiner*—Gwendolyn W. Baxter
*Attorney, Agent, or Firm*—Wood, Herron & Evans, L.L.P.

[57] ABSTRACT

A mounting structure (10) for facilitating the mounting of a medical device (20) to a support member (22). The medical device (20) includes a plate (28) having a downward facing device coupler (33). A connector (26) has a clamp (27) which is used to attach the connector (26) to the support member (22). The connector (26) further has an upward facing support coupler (34). The medical device (20) is initially hung from the connector (26) by engaging the device coupler (33) with the support coupler (34). In that partially coupled position, the medical device is stably supported on the support member but may be lifted therefrom. In addition, a latch (46) may be used to clamp the couplers (33, 34) together, thereby fully coupling the medical device (20) to the connector (26). With the latch (46) engaged, the medical device (20) is firmly engaged onto the connector (26).

33 Claims, 3 Drawing Sheets

U.S. PATENT DOCUMENTS

| | | | |
|---|---|---|---|
| 4,223,921 | 9/1980 | Goyne et al. | 285/266 |
| 4,340,199 | 7/1982 | Brock | 248/544 |
| 4,348,899 | 9/1982 | Muller | 73/431 |
| 4,410,095 | 10/1983 | Dembicks | 211/60 |
| 4,416,040 | 11/1983 | Towsley | 28/152 |
| 4,491,015 | 1/1985 | Allemano | 73/300 |
| 4,524,938 | 6/1985 | Strahs et al. | 248/110 |
| 4,547,092 | 10/1985 | Vetter et al. | 403/59 |
| 4,566,597 | 1/1986 | Caputo et al. | 211/87 |
| 4,597,291 | 7/1986 | Montomiya | 73/432 AD |
| 4,610,256 | 9/1986 | Wallace | 128/675 |
| 4,611,822 | 9/1986 | Bernhardson | 280/615 |
| 4,619,431 | 10/1986 | Matsui et al. | 248/500 |
| 4,620,736 | 11/1986 | Shanks | 293/116 |
| 4,674,722 | 6/1987 | Danby et al. | 248/231.3 |
| 4,688,864 | 8/1987 | Sorel | 439/74 |
| 4,691,710 | 9/1987 | Dickens et al. | 128/673 |
| 4,706,368 | 11/1987 | Crissman, III et al. | 29/526 R |
| 4,717,195 | 1/1988 | Okuyama et al. | 296/72 |
| 4,770,297 | 9/1988 | Chang | 206/379 |
| 4,776,343 | 10/1988 | Hubbard et al. | 128/675 |
| 4,832,294 | 5/1989 | Eidem | 248/125 |
| 4,832,299 | 5/1989 | Gorton et al. | 248/231.7 |
| 4,838,865 | 6/1989 | Flak et al. | 604/118 |
| 4,844,397 | 7/1989 | Skakoon et al. | 248/231.7 |
| 4,856,658 | 8/1989 | Novak | 211/13 |
| 4,903,929 | 2/1990 | Hoffman | 248/229 |
| 4,944,693 | 7/1990 | Puerner | 439/358 |
| 4,970,900 | 11/1990 | Shepherd et al. | 73/756 |
| 5,026,016 | 6/1991 | Lisowski | 248/314 |
| 5,035,389 | 7/1991 | Wang | 248/224.1 |
| 5,046,625 | 9/1991 | Rushing | 211/70.6 |
| 5,112,019 | 5/1992 | Metzler et al. | 248/405 |
| 5,155,663 | 10/1992 | Harase | 361/395 |
| 5,161,764 | 11/1992 | Roney | 248/231.7 |
| 5,174,533 | 12/1992 | Pryor et al. | 248/288.5 |
| 5,222,946 | 6/1993 | Kamen | 604/151 |
| 5,275,367 | 1/1994 | Frye | 248/205.3 |
| 5,280,789 | 1/1994 | Potts | 128/673 |
| 5,322,253 | 6/1994 | Stevens | 248/229.15 |
| 5,356,105 | 10/1994 | Andrews | 248/221.3 |
| 5,417,395 | 5/1995 | Fowler | 248/221.3 |

MEDICAL DEVICE MOUNTING STRUCTURE

FIELD OF THE INVENTION

The present invention relates generally to apparatus for supporting medical devices and, more particularly, to a mounting structure for hanging medical devices at a desired location.

BACKGROUND OF THE INVENTION

In hospital environments, many procedures involve inserting one or more catheters into a patient with lengths of tubing extending therefrom. Connected to the tubing may be a variety of medical devices such as transducers, flush valves, stop cocks and the like. Further, during any particular stay in the hospital, the types and numbers of medical devices being used with a patient is often changing. Also, as medical treatments become more sophisticated, so do the requirements of monitoring the patient's condition with different devices; and those devices will be used with a patient either singularly or in combinations with other devices.

Use of the devices requires that they be attached or mounted on a supporting structure. Such a structure includes, for example, vertical or horizontal poles, vertical or horizontal bed rails, specially designed supports in an operating room, etc. To accommodate such a great variety of mounting locations, a great number of different attachment devices have been developed. Further, the manufacturers of medical devices design their devices so that they can be mounted singularly or in clusters. To organize the devices and tubing associated therewith, it has been found beneficial to hold the devices to a mounting plate which in turn is secured to an intravenous pole or other nearby structure. Typically, such mounting plates have a flat surface with receptacles formed thereon for holding the medical devices in use as disclosed in the Stevens U.S. Pat. No. 5,322,253 and Shepherd el al. U.S. Pat. No. 4,970,900.

An other system for supporting various medical devices is to provide a modular system of interlocking plates as disclosed in the Fowler et al. U.S. Pat. No. 5,417,395 the disclosure of which is hereby incorporated by reference. Each plate has a receptacle for receiving a medical device and interlocking structure on the sides thereof to lock one plate with another and simulate a larger plate having receptacles for multiple medical devices. Such a system permits medical personnel to form any size plate necessary depending on the medical needs of the patient.

While the above systems function satisfactorily, they have some disadvantages. As illustrated by the above patents, one type of coupling is used to mount the medical devices on a common plate. In addition, a second different type of coupling is used to mount the common plate to the pole clamp which, in turn, is mounted to the pole. The different types and designs of couplings for mounting medical devices with different plates and mounting structures causes confusion in knowing what devices can be connected to what pole clamps or other connectors. Further, the differences coupling structures limit the interchangability of various devices and limit the combinations of devices that may exist and, in addition, increases the number of parts that must be inventoried in order to serve all combinations of needs all of which adds cost to the procedure.

SUMMARY OF THE INVENTION

The present invention provides a common modular mounting structure for easily hanging medical devices from a member or structure at a desired location. The invention simplifies the coupling of either a medical device or a plate containing medical devices to a pole clamp or other connector.

To this end and in accordance with the principles of the present invention, the mounting structure includes a component with a front side adapted to support a medical device element. The mounting structure further includes a device coupler on the rear side of the component. The device coupler has a first locating surface and a device cavity with a downward projecting device lip. The mounting structure also has a support coupler attachable to a supporting member. The support coupler has a second locating surface and a support cavity with a fixed and rigid upward projecting support lip. The cavities and lips are sized and shaped and positioned such that, upon the device coupler being moved to a rest position on the support coupler, the first and second locating surfaces are in a contacting relationship. Further, the downward projecting device lip extends into the support cavity and has an area of contact therewith, and the device cavity receives the upward projecting support lip and has an area of contact therewith. The couplers are cooperatively engaged to hold the component in the rest position on the supporting member and also to permit motion of the component away from the supporting member.

In one aspect of the invention the supporting member is a connector, such as a pole clamp for attaching the component in a fixed location, and the support coupler is located on a surface of the connector. In another aspect of the invention, the supporting member is a bracket, and the support coupler is located on one surface of the bracket for mounting the component and medical device element on the bracket. In addition, there is a second device coupler on another surface of the bracket that is identical to the device coupler on the component. The second device coupler engages with a second support coupler on a surface of a connector, such as a pole clamp, to mount the bracket to the pole clamp.

By virtue of the foregoing, there is thus provided a common modular mounting structure with the advantage of simply and easily hanging a medical device from a connector, such as a pole clamp, and thereafter, moving a latch to more securely lock the medical device in place. The same modular mounting structure is used to mount or hang several medical devices to a common plate, and those medical devices may thereafter be individually locked in place on the plate. Further, the same modular mounting structure is used to attach the common plate to the connector or pole clamp. Therefore, the modular mounting structure of the present invention has the advantage of eliminating the multiplicity of parts and different manipulations required by the different types of couplings of the prior art.

These and other objects and advantages of the present invention shall become apparent from the accompanying drawings and the detailed descriptions thereof.

BRIEF DESCRIPTION OF THE DRAWINGS

The accompanying drawings, which are incorporated in and constitute a part of the specification, illustrate embodiments of the invention and, together with a general description of the invention given above, and the detailed description given below, serve to explain the principles of the invention.

DETAILED DESCRIPTION OF THE DRAWINGS

Figure 1:
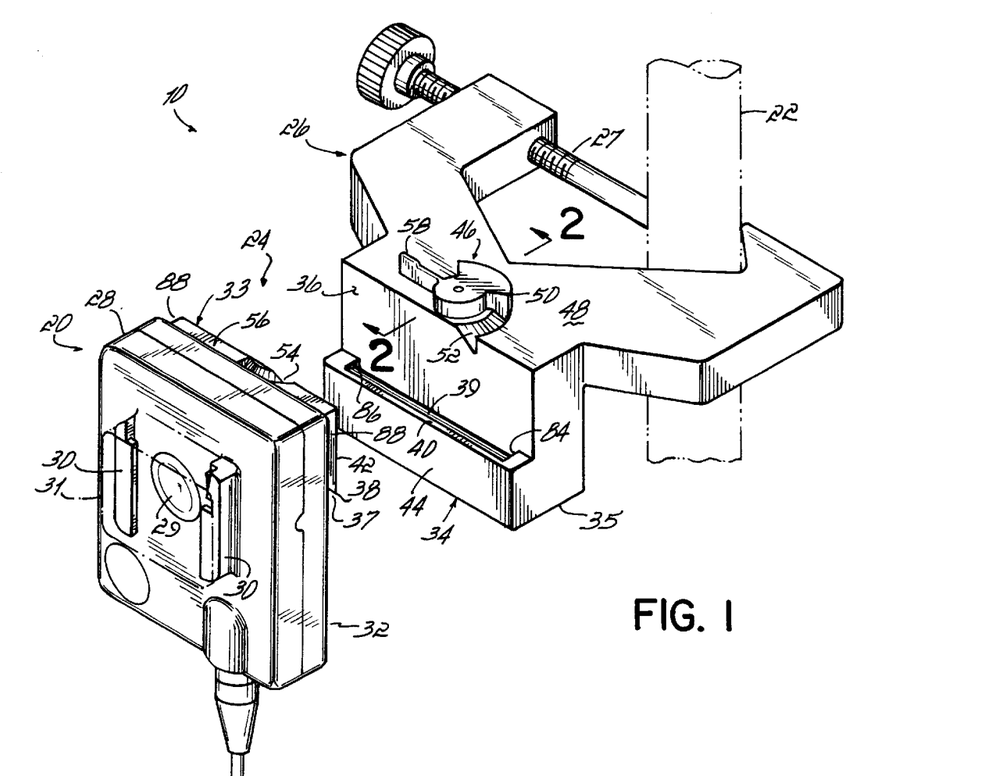
FIG. 1 is a disassembled perspective view of a mounting structure to facilitate mounting a medical device to a pole or other member in accordance with the principles of the present invention.
Figure 2:
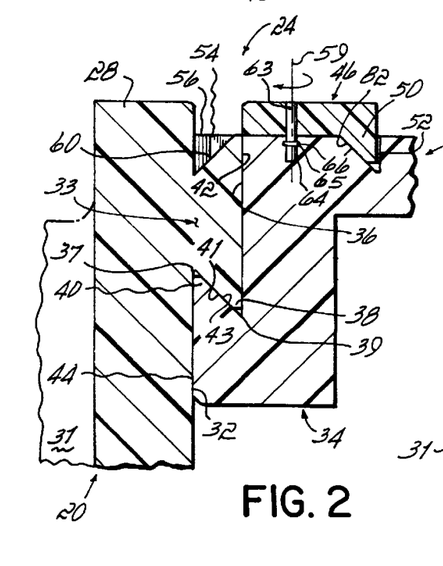
FIG. 2 is a cross-sectional view taken along line 2—2 of FIG. 1 and illustrates the medical device partially coupled to the connector.
Figure 3:
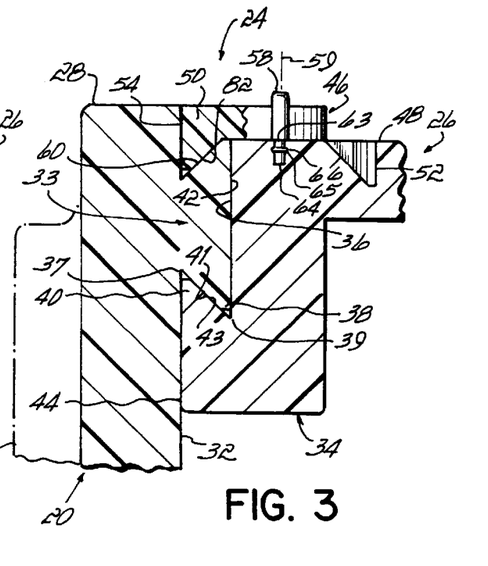
FIG. 3 is a cross-sectional view similar to FIG. 2 illustrating the medical device fully coupled to the connector.

Referring to FIGS. 1–3, mounting structure 10 is used to attach a component, for example, a medical device 20 to a pole or other structure 22. A coupling 24 is used to mount the medical device 20 to a connector 26, such as a pole clamp, which in turn is mounted to the pole 22 by means of a clamping device, for example, a screw clamp 27. The pole 22 can be a horizontal or vertical pole, a horizontal or vertical rail, a bed part, or any other mounting support; and the clamping device 27 can be any device for nonpermanently attaching one object to another object. The medical device 20 has a first component or rigid plate 28 which, in one embodiment, contains a reusable portion of a blood pressure transducer 29 integrated therein. The plate 28 further has a receptacle 30 for holding a medical device element such as a disposable sensor diaphragm 31 (shown in phantom) that is used with the reusable transducer portion 29. Combinations of reusable blood pressure transducers with disposable diaphragms are shown in U.S. Pat. No. 5,417,395 and a patent application entitled MODULAR MEDICAL PRESSURE TRANSDUCER and filed on even date herewith, the disclosures of both of which are hereby incorporated by reference.

The coupling 24 includes a device coupler 33 on a generally planar coupling surface 32 of the plate 28 and a mating support coupler 34 a body member or component 35 disposed on a planar mounting surface 32 of the connector 26. The device coupler 33 includes a downward facing cavity 37 with a downward projecting edge or lip 38; and the support coupler 34 includes an upward facing cavity 39 with an upward projecting fixed and rigid lip edge or lip 40. To achieve the partially coupled relationship illustrated in FIG. 2, the downward projecting lip 38 is hooked over the upward projecting lip 40, thereby hanging or suspending the plate 28 and medical device 20 from the connector 26.

In that hanging relationship, angular surface 41, extending from the downward facing cavity 37 to the downward projecting lip 38, is supported by surface 43, extending from the upward facing cavity 39 to the upward projecting lip 40. The upward projecting lip 40 and support coupler 34 provide a subjacent support for the downward projecting lip 38 and device coupler 33, respectively. Further, a first bearing surface 42 extending upward from the downward projecting lip 38 abuts against and has a common area of contact with a first forward surface 36 extending upward from the upward facing cavity 39. In addition, a second forward surface 44 extending downward from the upward projecting lip 40 abuts with and has a common area of contact with a bearing surface 32 extending downward from the downward facing cavity 37. The shape and size of the various areas of the above surfaces that are in a contacting relationship will depend on the extent to which those surfaces are designed to be in contact, their flatness, design specifications and manufacturing tolerances.

Generally and preferably, the greater the areas of contact between those opposing surfaces, the more securely the plate 28 and medical device 20 will be coupled to the connector 26. To maximize the areas of contact the outermost edges of the projecting lips 38, 40 should be sized and shaped so that they do not contact the bottoms of the respective cavities 37, 39. The above coupling configuration permits the plate 28 and medical device 20 to be placed on the connector 26 without having to manipulate locking mechanisms. Further, the hanging relationship of the medical device 20 and its plate 28 on the connector 26 permits the medical device 20 to be easily removed, relocated and otherwise manipulated.

The angled surface 43 of the upward facing cavity 39 provides a subjacent support for the device coupler 33 and prevents the plate 28 and medical device 20 from moving vertically downward. Points or an area of contact between the surface 42 forming one side of the lip 38 and surface 36 keep the device coupler 33 from moving in a direction generally perpendicular to the surface 36. Similarly, points or an area of contact between the surface 44 forming one side of the lip 40 with the surface 32 further stabilize the device coupler 33 with respect to the support coupler 34. Therefore, it is not necessary that the surfaces 36, 42 be in full contact, or that the surfaces 32, 44 be in full contact. The coupling 24 requires that the device coupler 33 have a surface that contacts a surface on the support coupler 34 over an area sufficiently large to provide the desired orientation of the device coupler 33 with respect to the support coupler 34. For example, the pairs of adjacent surfaces 41, 43 and 36, 42 and 32, 44 may either, as a single pair, or, in any combination of pairs, function as locating surfaces. The coupling 24 further requires that the device and support couplers 33, 34 have other points or lines of contact that are sufficient to stabilize the device coupler 33 in its hanging relationship on the support coupler 34.

To fully couple and further secure the medical device 20 onto the connector 26, the support coupler 34 further includes a latch 46 that is pivotally mounted on surface 48 which is generally perpendicular to the mounting surface 36. The latch 46 has a flange or cam 50 on a peripheral edge thereof which extends into a first arcuate groove 52 on the surface 48. The device coupler 33 has a second arcuate groove 54 which is disposed in a surface 56 that is generally perpendicular to the coupling surface 32. The second arcuate groove 54 is positioned to be contiguous with the first groove 52 when the medical device 20 is brought into a partially coupled and hanging relationship on the connector 26. As shown in FIG. 1, the lever arm 58 is then used to pivot or rotate the latch 46 such that the cam 50 is moved about an axis of rotation 59 and through the arcuate grooves 52, 54, thereby fully coupling and firmly securing the plate 28 and medical device 20 to the connector 26. The lever arm 58 extends radially and in a direction perpendicular to the axis of rotation of the latch 46. However, alternatively, the lever arm 58 may extend from the upper surface of the latch 46 in a direction parallel to the axis of rotation 59 of the latch 46.

FIG. 3 illustrates in more detail the structural relationships of the coupling 24 when the device coupler 33 is fully coupled to the support coupler 34. In that fully coupled relationship, the latch 46 is rotated until the cam 50 is moved into the second arcuate groove 54. To help locate the cam 50 as it enters the groove 54, preferably, the leading vertical and angled edges of the cam 50 are slightly rounded as will be the leading portion of the angular tip of the cam 50. The rotational motion of the latch 46 is facilitated by a shaft 63 that extends into a bore 64 in the surface 48 of the connector 26. To hold the latch 46 in the bore 64, the shaft 63 has an annular rib 65 that is disposed in an annular groove 66 in the bore 64. Alternatively, the latch 46 may be supported with respect to an axis of rotation by a screw or other fastener (not shown) that extends through a hole (not shown) in the coupler 34 and is attached to the latch. The screw provides the axis of rotation for the latch and cam, but the screw may or may not rotate with the latch.

Preferably, as the cam 50 pivots through the groove 54, the angular surface 82 of cam 50 bears against and applies a force against the angular surface 60 of the second arcuate groove 54. Therefore, the surface 82 on the cam 50 pushes on the surface 60 to further engage the downward projecting lip 38 into the upward projecting cavity 39, thereby more firmly engaging the device coupler 33 with the support coupler 34. When the latch 46 is in the position shown in FIG. 3, the associated plate 28 of medical device 20 cannot be lifted or removed from the connector 26. The surfaces 32, 41, 42, and 60 form a dovetail shaped coupling element on the medical device 20; and surfaces 36, 43, 44 and 82 form a mating dovetail shaped coupling element on connector 26. Therefore, when the plate 28 and medical device 20 are fully coupled to the support 22 with the latch 46 as shown in FIG. 3, the plate 28 and the medical device 20 cannot be inadvertently jostled or bumped off of the connector 26.

As will be appreciated, the cavities 37, 39, groove 54 and cam 50 can have other cross-sectional profiles, for example, curvilinear profiles, square profiles, etc.; and further, all of the profiles do not have to be identical or mate closely with each other as in the preferred embodiment. For example, the profiles of the cavity 39 may be curvilinear with a different radius from the profile of the lip 38 or the cavity 37. Alternatively, the pointed bottom of the cavity 39 may be replaced by a flat bottom, and surfaces 36 and 42 may flare or angle away from each other. Further, the lip 38 may be rounded, pointed or even have a square end.

The latch 46 prevents the plate 28 and medical device 20 from moving vertically upward. Referring back to FIG. 1, the support coupler 34 includes side walls 84, 86 at the ends of upward facing cavity 39 which are located adjacent the lateral sides 88 of the device coupler 33. Therefore, the inner directed surfaces of the side walls 84, 86 in the support coupler 120 on the plate bracket 112 block the device coupler 33 and associated plate 28 and medical device 20 from moving sideways in a longitudinal direction within the segmented portions of the cavity 39.

Figure 4:
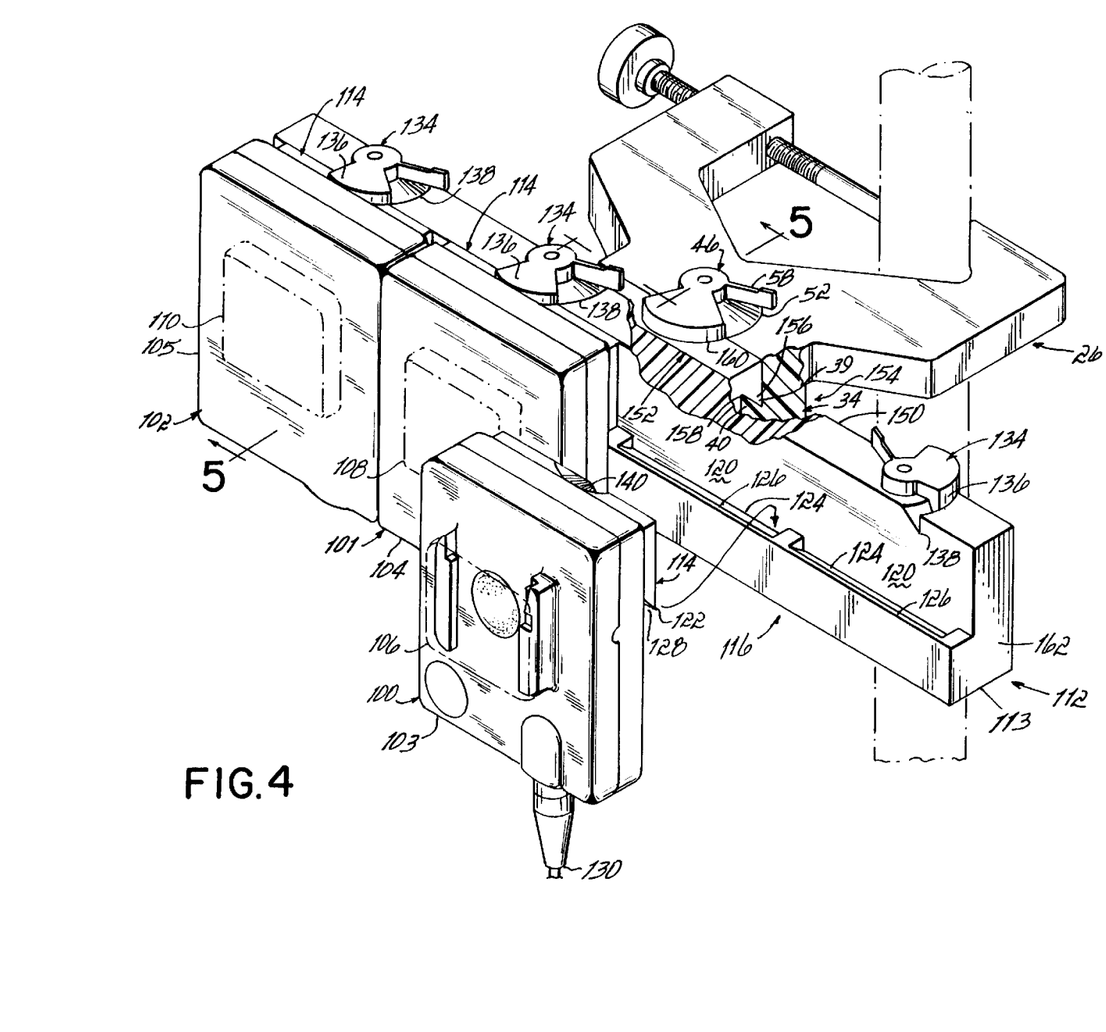
FIG. 4 is a perspective view with a cut away section of one alternative embodiment of the mounting structure in accordance with the principles of the present invention.
Figures 5, 6, 7, 8:
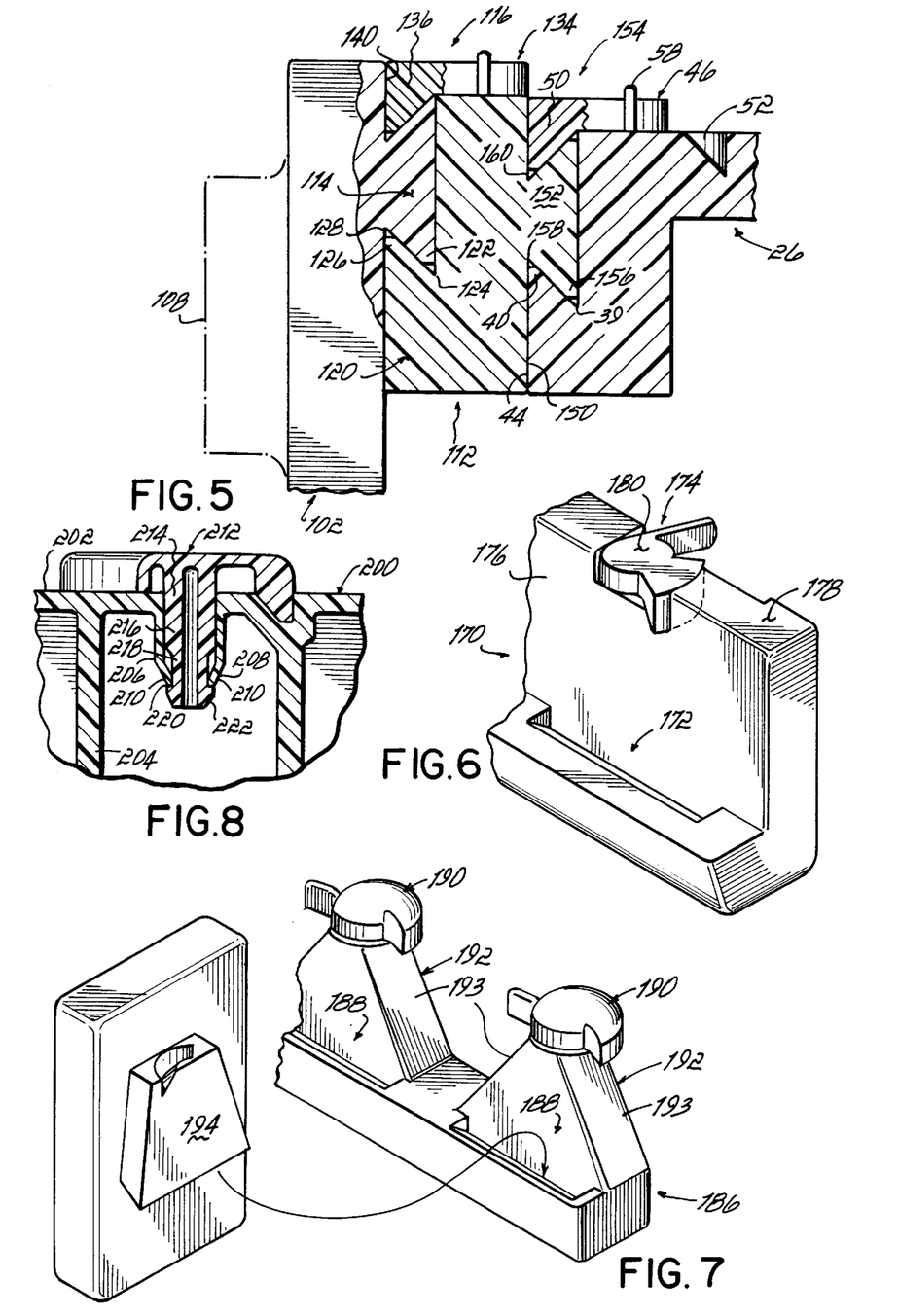
FIG. 5 is a cross-sectional view taken along line 5—5 of FIG. 4 and illustrates the medical device fully coupled to a plate bracket which, in turn, is fully coupled to the connector.
FIG. 6 is a partial perspective view illustrating another embodiment of the mounting structure in accordance with the principles of the present invention.
FIG. 7 is a partial perspective view illustrating a still further embodiment of the mounting structure in accordance with the principles of the present invention.
FIG. 8 is a partial cross-section view illustrating another alternative embodiment of the plate bracket and associated latch connection.

FIGS. 1–3 illustrate a mounting structure 10 for connecting a single plate 28 and medical device 20 to a support 26. However, many environments require that a plurality of medical devices be utilized; and further, it is considered to be convenient and efficient to mount the medical devices in batches or clusters. FIGS. 4 and 5 illustrate one embodiment for mounting a plurality of medical devices 100, 101, 102, which may be any combinations of the same or different medical devices. The medical devices 100, 101, 102 include a plurality of plates 103, 104, 105, respectively, which in turn support a plurality of medical device elements 106, 108, 110, respectively, to a single connector 26 by utilizing an intermediate plate bracket 112. Each of the plates 103, 104, 105 has a device coupler 114 of a coupling 116 identical to the coupling 24. Each of the device couplers 114 is identical in shape and construction to the first coupler 33 described with respect to FIGS. 1–3. Further, the plate bracket 112 has a body member 113 with support couplers 120 of the coupling 116. Each of the support couplers 120 is identical in shape and construction to the support coupler 34 described with respect to FIGS. 1–3. Therefore, any one or all of the plates 103, 104, 105 of the medical devices 100, 101, 102 can be partially coupled to the plate bracket 112 by simply inserting a respective downward extending projection 122 on each of the device couplers 114 into one of the grooves 124 of a respective one of the support couplers 120. When in the partially coupled position, each of the support couplers 114 has an upward projecting edge or lip 126 that engages a downward projecting cavity 128 of each of the device couplers 114. To more stably and securely hold one of the medical devices 100, 101, 102 to the plate bracket 112, a respective one of the latches 134 may be rotated or pivoted to move its cam 136 through a groove 138 in the plate bracket 112 and into a corresponding arcuate groove 140 in a respective one of the device couplers 114.

The plate bracket 112 has a coupling surface 150 on which is located a device coupler 152 of a coupling 154 identical to the couplings 24, 116. The device coupler 152 is identical in shape and construction to the device coupler 33 previously described. The device coupler 152 has a downward projecting lip 156 that engages the upward projecting cavity 39 on the connector 26. Further, the upward projecting lip 40 engages in a supporting relationship a downward facing cavity 158 of the device coupler 152, thereby partially coupling the plate bracket 112 onto the connector 26. The plate bracket 112 further has an arcuate groove 160 which is engaged by the cam 50 upon rotating the latch 46 to fully couple the plate bracket 112 to the connector 26.

FIG. 6 illustrates an alternative design of the plate bracket 112. Referring to FIG. 6, the plate bracket 170 has a support coupling member 172 identical to the support coupling member 120 of FIGS. 4 and 5; and latch 174 is identical in construction and operation to the latches 134 of FIGS. 4 and 5. The geometric shape of the plate bracket 170 is different from the plate bracket 112 in that the plate bracket 170 has a body portion 176 between the latches 174 having an outer surface 178 that is approximately coplanar with the outer surface 180 of the latch 174.

FIG. 7 illustrates a further alternative design of the plate bracket and the couplers. Referring to FIG. 7, the plate bracket 186 has a support coupling member 188 identical to the support coupling member 120 of FIGS. 4 and 5; and latch 190 is identical in construction and operation to the latches 134 of FIG. 4. The geometric shape of the plate bracket 186 is different from the plate bracket 112 in that the plate bracket 186 is cut away between the latches 190 to form generally triangular body portions 192 to support the latches 190, thereby reducing the amount of material used in the plate bracket 186. Preferably, the inclination of the side wall 193 of the body portion 192 matches the inclination and is an extension of the angled bottom surface within the groove 52 shown best in FIG. 1. Further, the device coupler 194 is made to have a shape generally matching the body portion 192 and further reduce the amount of material needed to make the device coupler 194.

FIG. 8 illustrates another construction of the plate bracket 200 which is manufactured or molded as a hollow part with an exterior wall 202 and internal ribs 204. Opposing tubular ears 206, 208 are secured on one end to the wall 202 and taper inwardly to form an opening at their distal ends 210 that is smaller in cross-section than the cross-sectional area between the ears at their upper end. The ears 206, 208 are able to flex apart in a radial direction with the greatest separation being at their distal ends. A latch 212 has a hollow shaft 214 extending therefrom that is sized and shaped to rotatably fit between the ears 206, 208. The shaft 214 has a first diameter at 216 and is necked to a smaller diameter over a central portion 218 of its length. The smaller diameter terminates at a shoulder 220 that extends radially outward to the first diameter and forms a knob 222 at the distal end of the shaft 214. When the shaft 214 is inserted between the ears 206, 208, the ears spread apart; until the knob 222 extends beyond the distal ends 210 of the ears 206, 208. The ears 206, 208 then collapse around the shaft 214; and the distal ends 210 of the ears 206, 208 move into the recess 218 of the shaft 214. The distal ends 210 of the ears 206, 208 are then adjacent the shoulder 220 of the knob 222 which secures the latch 212 in its desired position and prevents the latch from being removed from the plate bracket 200.

In use, referring to FIGS. 1 and 4, an appropriate mounting structure is identified, for example, the IV pole 22, and a connector such as the pole clamp 26 is fixed to the pole 22. If the medical device to be used is a reusable component of a pressure transducer as described in the previously referenced and incorporated patent application entitled MODULAR MEDICAL PRESSURE TRANSDUCER, the appropriate disposable transducer element 31 is mounted on the structure 30. As is well known, stop cocks, tubing and a catheter can be attached to the disposable element 31. Thereafter, the device coupler 33 is inserted into the support coupler 34 so that the medical device 20 is partially coupled or hung from a connector 26. While in the partially coupled mode, to remove the medical devices 20 from the connector 26, it is simply lifted therefrom. Therefore, the medical device is easily handled and manipulated in the partially coupled position. When it is desired to more firmly hold the medical devices in place, that is, in a more secure, fully coupled mode, the latch 46 on the connector 26 is rotated to selectively engage the arcuate slot 54 of device coupler 33. When the medical device 20 is fully coupled to the connector 26, it cannot be lifted therefrom, nor can it be dislodged by inadvertent bumps or manipulation of the connector 26. When fully coupled to the support 26, the medical device 20 is then coupled to tubing or other elements of the patient care system; and the disposable element 31 can be changed, etc. At any time, the medical device 20 can be removed from the connector 26 by rotating the latch 46 to disengage the groove 54, so that the medical device can be lifted and removed from the connector 26.

If more than one medical device is to be used as illustrated in FIGS. 4 and 5, the device coupler 152 is inserted into the support coupler 34 of the connector 26. Preferably, the latch 46 is rotated to fully engage the coupling 154 and firmly hold the plate bracket 112 on the connector 26. Thereafter, other medical devices 100, 101, 102 are hung on the plate bracket by inserting their respective device couplings 114 into the support couplings 120 on the plate bracket 112. When partially coupled, medical devices 100, 101, 102 may be easily rearranged, exchanged, or removed by simply lifting the medical device therefrom. As previously described, the medical devices are fully coupled to the plate bracket 112 by rotating the latches 134 to engage cams 136 in respective grooves 140. With the present invention, the same coupling structure is used to couple the plate bracket 112 to the connector 26 and the medical devices 100, 101, 102 to the plate bracket 112. The coupling is of a simple construction that provides a first partially coupled mode for holding the devices in a hanging removable posture and, a second, fully coupled mode in which the devices are firmly held onto the plate bracket 112. By having both couplings 116, 154 identical and simple, the inventory of special coupling pieces is reduced.

While the invention has been set forth by a description of the preferred embodiments in considerable detail, it is not intended to restrict or in any limit the claims to such detail. Additional advantages and modifications will readily appear to those who are skilled in the art. For example, the plate 28 is described as having a medical device 29 integrated therein with an element attachable thereto. Alternatively, the entire medical device may be mounted on the receptacle 30. Further, the connector 26 is illustrated as having a single support coupler mounted opposite the clamp. Alternatively, the connector may have a plurality of mounting surfaces with device couplers and respective latches. Those surfaces may be located in opposition with each other, perpendicular with each other, or in any other designed orientation. Further, the clamping device may be in any designed orientation and positional relationship to the one or more mounting surfaces.

As illustrated in FIG. 3, the support coupler includes a latch 46 having an angled cam 50 that rotates through an arcuate groove 54. As will be appreciated, the grooves 52, 54 can be removed; and the cam 50 of the latch 46 can be replaced by a generally planar lower surface that moves adjacent the generally flat surface 56 on the device coupler 33. That lower surface can further include one or more projecting elements which may be in the form of a projecting ring that contacts the surface 56 to apply a force against the device coupler 33, thereby further engaging it within the support coupler 34. Alternatively, the projecting element may be one or more bumps or protrusions that extend from the lower surface of the latch toward the surface 56. Further, the surface 56 may include a recess for receiving one of the bumps to define a stop position for the latch. As will be appreciated, a latching force may be created by other mechanisms such as a ball detent located in the device coupler 33. Alternatively, the fully coupled relationship of the device coupler 33 with the support coupler 34 may be created without using any projection from the latch 46, and the lower surface of the latch 46 may move immediately adjacent the surface 56. Those surfaces may or may not be in a contacting relationship. Even if there is no contact in relationship, the latch 46 is still effective to prevent the device coupler 33 from being removed from the support coupler 34.

As shown in FIG. 4, the plate bracket 112 has a longitudinal mounting surface containing a plurality of the support couplers 120 for receiving a plurality of medical devices. Alternatively, the plate bracket 112 may have support couplers on mounting surfaces which are on the ends 162 of the plate bracket 112. Consequently, another plate bracket which is identical to the plate bracket 112, may either be partially coupled to an end 162 of the bracket 112, or, using a latch, fully coupled thereto. As will further be appreciated, the plate bracket may be constructed with several parts that are movable with respect to each other. For example, they can pivot like a hinge or rotate about a central axis with respect to each other, so that the medical device(s) can be mounted in any orientation with respect to the pole or other supporting member.

The invention in its broadest aspects is therefore not limited to the specific details and representative and illustrated examples shown and described. Accordingly, departures may be made from the details described herein without departing from the spirit and scope of applicants' general inventive concept.

What is claimed is:

1. A medical device mounting structure comprising:
   a first component having a front side being adapted to support a medical device element;
   a device coupler on a rear side of the first component, the device coupler having a first locating surface and a downward facing cavity with a downward projecting lip;
   a second component adapted to be connected to a supporting member:
   a support coupler on the second component, the support coupler having a second locating surface and an upward facing cavity with a fixed and rigid upward projecting lip, the upward facing cavity and the upward projecting lip being fixed with respect to the second component; and
   the cavities and the lips being shaped and positioned such that, upon the device coupler being placed on the support coupler in a rest position, the first and second locating surfaces abut each other in a contacting relationship, the downward projecting lip extends into the upward facing cavity and has an area of contact therewith, the downward facing cavity receives the upward projecting lip and has an area of contact therewith, and the device coupler and the support coupler are cooperatively engaged to hang the first component in the rest position on the supporting member, and to permit the first component to be lifted from the supporting member.

2. The medical device mounting structure of claim 1 wherein the first component includes a reusable portion of a pressure transducer.

3. The medical device mounting structure of claim 1 wherein the supporting member comprises a connector for attaching the first component at a fixed location, and the second component is located on a surface of the connector.

4. The medical device mounting structure of claim 3 wherein the connector is a pole clamp attachable to a pole.

5. The medical device mounting structure of claim 4 further comprising:
   a groove extending across a surface of the device coupler; and
   the latch having a flange extending therefrom and sized and shaped to fit into the groove, whereby upon mounting the device coupler on the support coupler and moving the latch to the first position moves the flange into the groove, thereby creating the blocking relationship, and moving the latch to the second position moves the flange out of the groove, thereby creating the nonblocking relationship.

6. The medical device mounting structure of claim 5 wherein the latch is on the support coupler and the groove extends continuously across surfaces of the device and the support coupler; and upon mounting the device coupler on the support coupler and moving the latch to the first position, the flange moves from a portion of the groove located in the support coupler into a portion of the groove located in the device coupler, thereby creating the blocking relationship, and upon moving the latch to the second position the flange moves out of the portion the groove located in the device coupler and into the portion of the groove located in the support coupler, thereby creating the nonblocking relationship.

7. The medical device mounting structure of claim wherein 6 the flange has a cam surface that contacts and pushes on a surface in the portion of the groove in the device coupler upon the latch being moved to the first position, thereby more firmly locking the device and support couplers together.

8. The medical device mounting structure of claim 6 wherein a cross-section of the groove in the device coupler and a cross-section of the flange on the latch have mating angular shapes.

9. The medical device mounting structure of claim 8 wherein cross-sections of the upward facing cavity and the downward projecting lip, cross-sections of the downward facing cavity and the upward projecting lip and cross-sections of the groove in the device coupler and the flange on the latch collectively have a mating dovetail shape.

10. The medical device mounting structure of claim 1 wherein the supporting member further comprises a bracket, and the second component is located on one surface of the bracket.

11. The medical device mounting structure of claim 10 wherein the bracket has a second device coupler located on another surface of the bracket, the second device coupler being identical to the device coupler on the rear side of the first component.

12. The medical device mounting structure of claim 11 further comprising a connector attachable at a fixed location and having a second support coupler on a surface thereof, the second support coupler being identical with the support coupler on the bracket, the second device coupler being engageable with the second support coupler to place the bracket on the connector at the fixed location, and the device coupler on the first component being engageable with the support coupler on the bracket to place the first component on the bracket at the fixed location.

13. The medical device mounting structure of claim 1 wherein the area of contact between the upward facing cavity and the downward projecting lip is between a bearing surface extending generally in the upward direction from the downward projecting lip and a forward surface extending generally in the upward direction from the upward facing cavity.

14. The medical device mounting structure of claim 1 wherein the are a of contact between the downward facing cavity and the upward projecting lip is between a bearing surface extending generally in the downward direction from the downward facing cavity and a forward surface extending generally in the downward direction from the upward projecting lip.

15. The medical device mounting structure of claim 1 wherein the first locating surface extends from the downward facing cavity out to the downward projecting lip, and the second locating surface extends from the upward facing cavity out to the upward projecting lip.

16. The medical device mounting structure of claim 1 wherein the device and the support coupler has a latch for holding the coupler in the rest position.

17. The medical device mounting structure of claim 16 wherein the latch is movable between a first position preventing the device coupler from being removed from the support coupler, and a second position permitting the device coupler to be removed from the support coupler.

18. The medical device mounting structure of claim 12 wherein the latch is pivotally mounted on the support coupler, the latch having a blocking relationship with respect to the device coupler in response to the latch being in the first position, and the latch having a nonblocking relationship with respect to the device coupler in response to the latch being in the second position.

19. The medical device mounting structure of claim 1 wherein the upward facing cavity in the support coupler has a length to permit the upward facing cavity to receive a plurality of downward projecting lips on a plurality of device couplers, upon the plurality of device couplers being mounted in a rest position on the support coupler.

20. The medical device supporting structure of claim 19 wherein the support coupler further includes a plurality of latches, each being association with one of the plurality of device couplers.

21. The medical device mounting structure of claim 1 wherein the support coupler has a plurality of upward facing cavities extending over its length, each of the plurality of upward facing cavities being sized and shaped to generally receive the downward projecting lip on a device coupler.

22. The medical device mounting structure of claim 1 wherein cross-sections of the upward facing cavity and the downward projecting lip and cross-sections of the downward facing cavity and the upward projecting lip have generally mating angular shapes.

23. An attachment for supporting a medical device comprising:
an attachment device adapted to be connected to a member; and
a support coupler having
a body member connected to the attachment device,
a locating surface adapted to contact a locating surface on a mating device coupler supporting a medical device, and
a generally upward facing cavity with a fixed and rigid upward projecting lip, the upward facing cavity and the lip being fixed with respect to the body member, the upward facing cavity being adapted to receive a downward projecting lip on the device coupler and the upward projecting lip being adapted to extend into a downward facing cavity on the device coupler to hang the medical device in a rest position on the support coupler and, to permit the medical device to be lifted from the support coupler.

24. A medical device component comprising:
a rigid plate having first and second sides;
a medical device element associated with the first side of the plate; and
a device coupler associated with the second side of the plate and having
a locating surface adapted to contact another locating surface of a support coupler attached to a supporting member for supporting the plate at a desired location, the support coupler having an upward facing cavity and upward projecting lip fixed thereto, and
a downward facing cavity with a fixed and rigid downward projecting lip, the downward facing cavity adapted to receive the upward projecting lip of the support coupler, the downward projecting lip adapted to extend into the upward facing cavity of the support coupler to hang the plate at a rest position on the supporting member, and to permit the plate to lifted from the supporting member.

25. A medical device support bracket comprising:
a plate having opposed first and second sides;
a support coupler having a body member located on the first side of the plate and having
a locating surface adapted to mate with a surface on a mating device coupler, and
an upward facing cavity with an upward projecting lip, the upward facing cavity adapted to receive a mating downward projecting lip of the mating device coupler and the upward projecting lip adapted to extend into a mating downward facing cavity of the mating device coupler, the upward facing cavity and the upward projecting lip being fixed with respect to the body member; and
a device coupler located on the second side of the plate and having
a first locating surface adapted to mate with a surface on a mating support coupler, and
a downward facing cavity with a fixed and rigid downward projecting lip, the downward facing cavity adapted to receive a mating upward facing lip of the mating support coupler and downward projecting lip adapted to extend into a mating upward facing cavity of the mating support coupler.

26. A mounting structure to facilitate attaching a medical device to a member comprising:
a device coupler adapted to support the medical device, the device coupler having a downward projecting lip;
a support coupler adapted to be mounted to the member, the support coupler having an upward facing cavity for receiving the downward projecting lip of the device coupler;
a latch operably connected to the support coupler, the latch being movable to a first position in a confronting relationship with the upward facing cavity, thereby blocking the device coupler from being moved away from the support coupler and releasably securing the medical device to the member, and the latch being movable to a second position out of the confronting relationship with the upward facing cavity, thereby permitting the device coupler with the medical device to be moved away from the support coupler on the member.

27. A medical device mounting structure comprising:
a component having a front side being adapted to support a medical device element;
a device coupler on a rear side of the component, the device coupler having a first locating surface and a downward facing cavity with a downward projecting lip;
a rigid support coupler adapted to be attached to a supporting member, the support coupler having a second locating surface and an upward facing cavity with a fixed and rigid upward projecting lip, the upward facing cavity and the upward projecting lip being fixed with respect to the support coupler; and
the cavities and the lips being shaped and positioned such that, upon the device coupler being placed on the support coupler in a rest position, the first and second locating surfaces abut each other in a contacting relationship, the downward projecting lip extends into the upward facing cavity and has an area of contact therewith, the downward facing cavity receives the upward projecting lip and has an area of contact therewith, and the device coupler and the support coupler are cooperatively engaged to hang the component in the rest position on the supporting member, and to permit the component to be lifted from the supporting member.

28. A medical device mounting structure comprising:
a component having a front side being adapted to support a medical device element;

a device coupler on a rear side of the component, the device coupler having a first locating surface and a downward facing cavity having a first surface oblique with respect to a side of the component and extending to a downward projecting lip;

a support coupler adapted to be attached to a supporting member, the support coupler having a second locating surface and an upward facing cavity having a second surface oblique with respect to a side of the support coupler and extending to a fixed and rigid upward projecting lip, the upward facing cavity and the upward projecting lip being fixed with respect to the support coupler; and the cavities and the lips being shaped and positioned such that, upon the device coupler being placed on the support coupler in a rest position, the first and second locating surfaces abut each other in a contacting relationship, the downward projecting lip extends into the upward facing cavity and has an area of contact therewith, the downward facing cavity receives the upward projecting lip and has an area of contact therewith, the first and second surfaces are in juxtaposition and the device coupler and the support coupler are cooperatively engaged to form a hanging support for the device coupler to hang the component in the rest position on the supporting member, and to permit the component to be lifted from the supporting member.

29. A medical device for coupling a medical device element on a supporting member mounting structure comprising:

a component having a front side being adapted to support the medical device element;

a device coupler on a rear side of the component, the device coupler having a first locating surface and a downward facing cavity with a downward projecting lip;

a bracket having a support coupler located on one surface of the bracket, the bracket adapted to be attached to the supporting member, the support coupler having a second locating surface and an upward facing cavity with a fixed and rigid upward projecting lip; and the cavities and the lips being shaped and positioned such that, upon the device coupler being placed on the support coupler in a rest position, the first and second locating surfaces abut each other in a contacting relationship, the downward projecting lip extends into the upward facing cavity and has an area of contact therewith, the downward facing cavity receives the upward projecting lip and has an area of contact therewith, and the device coupler, and the support coupler are cooperatively engaged to form a hanging support for the device coupler to hang the component in the rest position on the supporting member, and to permit the component to be lifted from the supporting member.

30. A mounting structure comprising:

an attachment device adapted to be connected to a member;

a support coupler on one side of the attachment plate having a fixed, rigid, upward projecting lip, a surface extending obliquely toward the one side of the attachment device to form a generally upward facing cavity between the upward projecting lip and the one side of the attachment device, and two generally vertical surfaces being generally perpendicular with the one side of the attachment device to provide two locating surfaces with respect to the generally upward facing cavity, the upward facing cavity being shaped and adapted to receive a downward projecting lip of a device coupler moving downward into the upward facing fixed cavity and the upward projecting lip being shaped and adapted to receive a downward projecting cavity of the device coupler moving downward over the upward projecting lip, thereby hanging the device coupler at a rest position on the support coupler but permitting the device coupler to be lifted from the support coupler.

31. A mounting structure comprising:

a plate having first and second sides;

a medical device element associated with the first side of the plate; and a device coupler on the second side of the plate and having a rigid downward projecting lip, and a first surface adapted to contact a locating surface of a support coupler attached to a supporting member for supporting the plate at a desired location, and a second surface extending obliquely toward the second side of the plate to form a generally downward facing cavity between the downward projecting lip and the second side of the plate, the device coupler being shaped, so that, as the downward facing cavity of the device coupler moves downward onto an upward projecting fixed lip of the support coupler, the downward projecting lip of the device coupler moves downward into an upward facing fixed cavity of the support coupler, and the first surface on the device coupler bears against the locating surface on the support coupler, thereby hanging the plate at a rest position on the supporting member but permitting the plate to be lifted from the supporting member.

32. A mounting structure comprising:

an attachment device adapted to be connected to a member and having a support coupler on one side of the attachment device, the support coupler having an upward projecting lip and a first surface extending obliquely toward one side of the attachment device to form a generally upward facing cavity between the upward projecting lip and the one side of the attachment device; and a plate having first and second sides with a medical device element associated with the first side and a device coupler on the second side, the device coupler having a downward projecting lip and a second surface extending obliquely toward a second side of the plate to form a generally downward facing cavity between the downward projecting lip and the second side of the plate, the downward projecting lip of the device coupler being engageable with the upward facing cavity of the support coupler and the upward projecting lip of the support coupler being simultaneously engageable with the downward facing cavity of the device coupler such that the first surface of the support coupler guides the downward projecting lip of the device coupler downward and toward the one side of the attachment device to bring and maintain at least two pairs of surfaces on the couplers in a bearing relationship with respect to each other.

33. A mounting structure comprising:

an attachment device adapted to be connected to a member and having a support coupler on one side of the attachment device, the support coupler including an upward projecting lip having a first nonrectangular cross-section and forming a generally upward facing cavity having a second nonrectangular cross-section; and a plate having first and second sides with a medical device element associated with the first side and a device coupler on the second side, the device coupler including a downward projecting lip having a nonrectangular cross-section generally complementary to the second nonrectangular cross-section of the upward facing cavity, the downward projecting lip forming a generally downward facing cavity with the second side of the plate, and the downward facing cavity having a nonrectangular cross-section generally complementary with the first nonrectangular cross-section of the upward projecting lip, the downward projecting lip of the device coupler being engageable with the upward facing cavity of the support coupler and the upward projecting lip of the support coupler being simultaneously engageable with the downward facing cavity of the device coupler to, in response to gravity, force the device coupler linearly vertically downward and linearly horizontally toward the support coupler to hang the device coupler on the support coupler with a locating surface on the support coupler bearing against a respective mating locating surface on the device coupler.

* * * * *

UNITED STATES PATENT AND TRADEMARK OFFICE
CERTIFICATE OF CORRECTION

PATENT NO. : 5,829,723
DATED : Nov. 3, 1998
INVENTOR(S) : Brunner et al.

It is certified that error appears in the above-identified patent and that said Letters Patent is hereby corrected as shown below:

In column 1, line 38, delete "el" and insert therefor --et--.

In column 1, line 59, delete "interchangability" and insert therefor --interchangeability--.

In column 8, line 10, after "any", insert --way--.

In the Claims

In Claim 7, column 10, line 2, delete "wherein 6" and insert therefor --6 wherein--.

In Claim 23, column 11, line 34, before "lip", insert --upward projecting--.

In Claim 20, column 11, line 9, delete "supporting".

Signed and Sealed this

Twenty-ninth Day of June, 1999

Attest:

Q. TODD DICKINSON

*Attesting Officer*  *Acting Commissioner of Patents and Trademarks*